United States Patent
Meyer et al.

(10) Patent No.: US 7,186,237 B2
(45) Date of Patent: Mar. 6, 2007

(54) BALLON CATHETER FOR CREATING A LONGITUDINAL CHANNEL IN A LESION AND METHOD

(75) Inventors: Steven T. Meyer, San Jose, CA (US); Wayne M. Ogata, San Ramon, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 343 days.

(21) Appl. No.: 10/075,630

(22) Filed: Feb. 14, 2002

(65) Prior Publication Data

US 2003/0153870 A1    Aug. 14, 2003

(51) Int. Cl.
*A61M 29/00* (2006.01)
(52) U.S. Cl. .................................................. 604/96.01
(58) Field of Classification Search ............. 604/96.01, 604/101.01–101.05, 915, 916, 917, 918, 604/919, 921; 606/191–194
See application file for complete search history.

(56) References Cited

U.S. PATENT DOCUMENTS

| | | | |
|---|---|---|---|
| 2,854,983 A | 10/1958 | Baskin | |
| 4,790,812 A | 12/1988 | Hawkins, Jr. et al. | |
| 4,983,167 A | 1/1991 | Sahota | |
| 5,158,564 A | 10/1992 | Schnepp-Pesch et al. | |
| 5,196,024 A * | 3/1993 | Barath | 606/159 |
| 5,320,634 A * | 6/1994 | Vigil et al. | 606/159 |
| 5,336,178 A * | 8/1994 | Kaplan et al. | 604/509 |
| 5,336,234 A | 8/1994 | Vigil et al. | |
| 5,338,300 A | 8/1994 | Cox | |
| 5,350,361 A | 9/1994 | Tsukashima et al. | |
| 5,556,408 A | 9/1996 | Farhat | |
| 5,575,771 A | 11/1996 | Walinsky | |
| 5,616,149 A | 4/1997 | Barath | |
| 5,628,746 A | 5/1997 | Clayman | |
| 5,713,913 A | 2/1998 | Lary et al. | |
| 5,797,935 A | 8/1998 | Barath | |
| 5,863,284 A * | 1/1999 | Klein | 600/3 |
| 5,904,679 A | 5/1999 | Clayman | |
| 5,954,742 A | 9/1999 | Osypka | |
| 5,967,984 A | 10/1999 | Chu et al. | |
| 6,136,014 A | 10/2000 | Sirimanne et al. | |
| 2002/0010489 A1 | 1/2002 | Grayzel et al. | |

* cited by examiner

*Primary Examiner*—Manuel Mendez
(74) *Attorney, Agent, or Firm*—Dorsey & Whitney LLP

(57) ABSTRACT

A balloon catheter for performing an angioplasty procedure on a lesion in a vessel comprising a flexible elongate catheter shaft having proximal and distal extremities. A balloon is secured to the distal extremity of the catheter shaft and has an outer surface extending between proximal and distal extremities of the balloon. A flexible elongate element is provided which extends over the outer surface of the balloon. The flexible elongate element has proximal and distal extremities which are secured about the catheter shaft in positions spaced longitudinally away from the outer surface of the balloon to permit expansion of the balloon and to cause movement of the flexible elongate element into engagement with the lesion to form a longitudinal channel in the lesion.

25 Claims, 3 Drawing Sheets

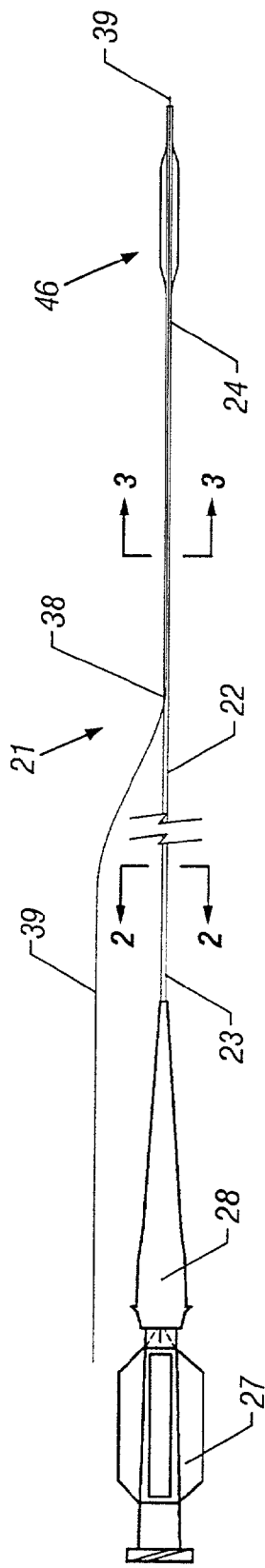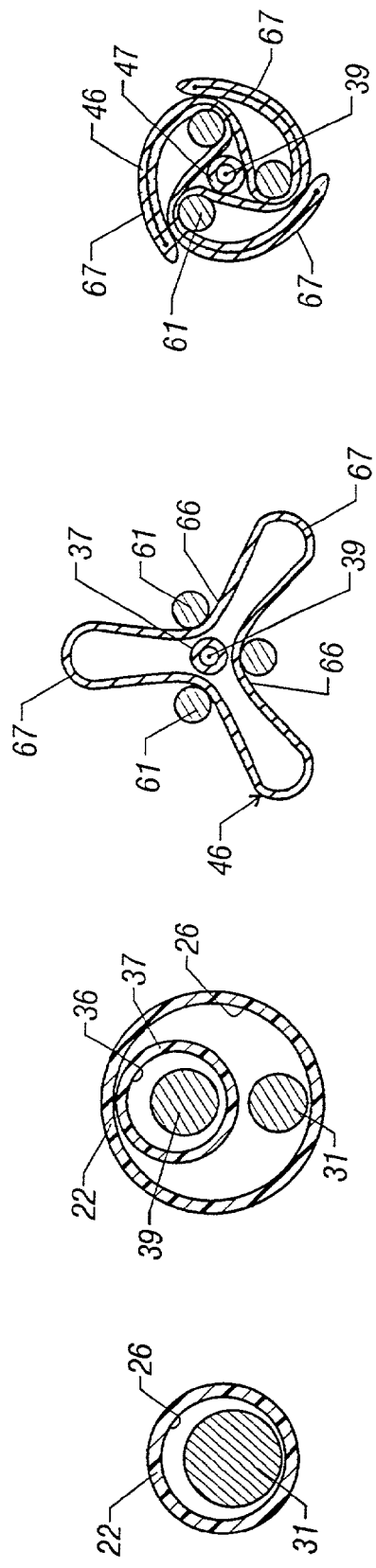

BALLON CATHETER FOR CREATING A LONGITUDINAL CHANNEL IN A LESION AND METHOD

This invention relates to a balloon catheter for creating a longitudinal channel in a lesion and a method for constructing the balloon catheter.

Balloon catheters have heretofore been provided which have knives mounted on the balloon such as disclosed in U.S. Pat. Nos. 5,196,024, 5,320,634, 5,616,149 and 5,797,935. Such devices have been found to have disadvantages in that a special mounting must be provided for securing the knives to the balloon. There is a potential for such knives becoming detached from the balloon. In other embodiments, the knives are seated within longitudinal grooves provided in the balloon. Such approaches decrease the flexibility of the balloon and in addition increase the costs of construction. There is therefore a need for a new and improved balloon catheter which overcomes these disadvantages.

In general, it is an object of the present invention to provide a balloon catheter for creating a longitudinal channel in a lesion and a method for making the balloon catheter.

Another object of the invention is to provide a balloon catheter and a method of the above character in which flexible elongate elements are utilized which are urged radially by the balloon for creating longitudinal channels in the lesion.

Another object of the invention is to provide a balloon catheter of the above character which aids in inhibiting longitudinal movement of the balloon during inflation.

Another object of the invention is to provide a balloon catheter and method of the above character in which the flexible elongate elements can be readily deployed.

Another object of the invention is to provide a balloon catheter of the above character in which the flexible elongate elements are flexible to facilitate passage through tortuous vessels.

Another object of the invention is to provide a balloon catheter of the above character which can be economically manufactured.

Additional objects and features of the invention will appear from the following description in which the preferred embodiments are set forth in detail in conjunction with the accompanying drawings.

FIG. 1 is a side elevational view of a balloon catheter incorporating the present invention.

FIG. 2 is an enlarged cross sectional view taken along the line 2—2 of FIG. 1.

FIG. 3 is an enlarged cross sectional view taken along the line 3—3 of FIG. 1.

FIGS. 4 and 5 are cross sectional views taken along the line 5—5 of FIG. 1 with FIG. 4 showing the balloon prior to folding over wings or flaps and with FIG. 5 showing the balloon folded over the flexible elongate elements so that the elongate elements will not damage the vessel during placement in the vessel.

Figure 6:
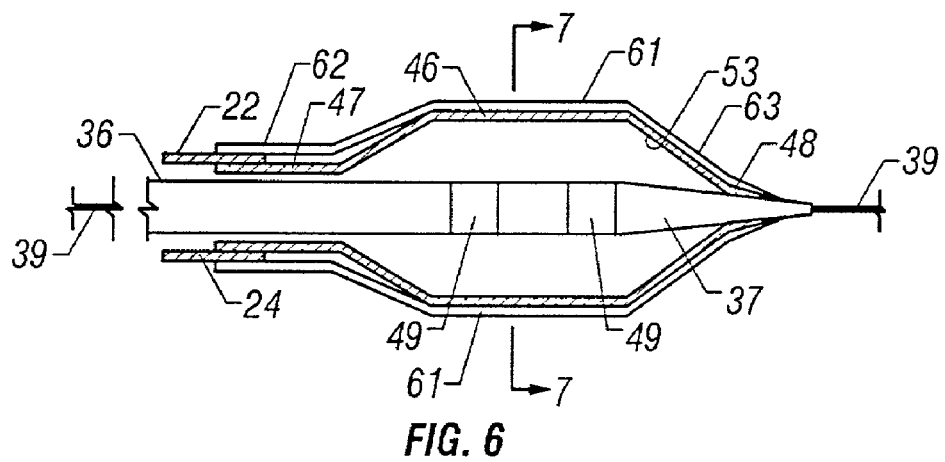
FIG. 6 is an enlarged distal extremity of the balloon catheter shown in FIG. 1 showing the balloon in an inflated condition.
Figure 7:
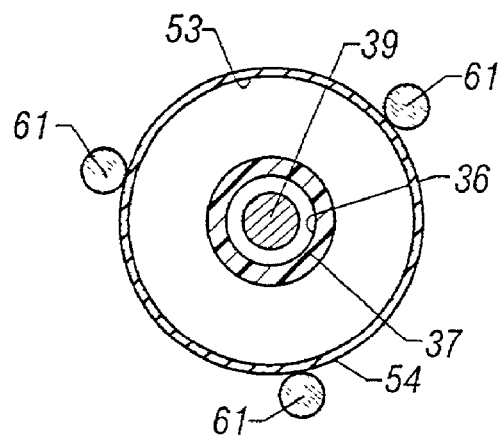
FIG. 7 is a cross sectional view taken along the line 7—7 of FIG. 6.
Figure 8:
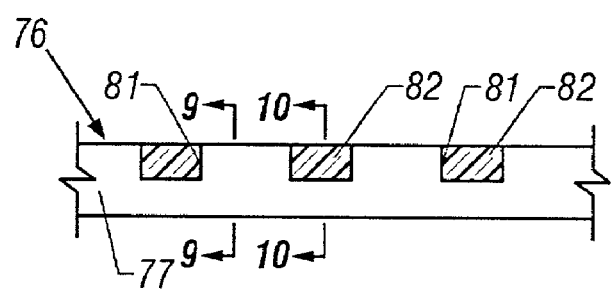
FIG. 8 is an enlarged elongate portion of an alternative flexible elongate element for use with a balloon catheter in accordance with the present invention.

In general, the balloon catheter is for performing an angioplasty procedure on a lesion in a vessel. The balloon catheter comprises a flexible elongate catheter shaft having proximal and distal extremities. A balloon is secured to the distal extremity of the catheter shaft and has proximal and distal extremities and has an interior and is movable between deflated and inflated conditions. The catheter shaft has a balloon inflation lumen extending from the proximal extremity to the distal extremity of the catheter shaft and opening into the interior of the balloon. A fitting is provided for supplying an inflation medium to the inflation lumen for causing movement of the balloon from the deflated condition to the inflated condition. The balloon has an outer surface extending from the proximal extremity to the distal extremity of the balloon which moves outwardly radially upon inflation of the balloon. A flexible elongate element extends over the outer surface of the balloon from the proximal extremity to the distal extremity of the balloon. The flexible elongate element has proximal and distal extremities which are secured about the catheter shaft in positions spaced away from the outer surface of the balloon to permit expansion of the balloon and to thereby cause movement of the flexible elongate element into engagement with the lesion to form a longitudinal channel in the lesion.

More in particular as shown in FIGS. 1–7 of the drawings, the balloon catheter 21 of the present invention consists of a catheter shaft 22 which is provided with proximal and distal extremities. The catheter shaft 22 is formed in a conventional manner such as by the use of an extruded polymer tubing and having a diameter ranging from 0.020" to 0.070" and preferably about 0.035" and typically having a length of 50 to 150 cm and preferably about 135 cm. The catheter shaft 22 is typically provided with a hydrophilic coating (not shown) to reduce friction. A balloon inflation lumen 26 is provided in the catheter shaft 22 which extends from the proximal extremity 23 to the distal extremity 24 of the catheter shaft 22. A Luer type fitting 27 is secured to the proximal extremity 23 of the catheter shaft 22 and is secured thereto by a strain relief 28.

A core wire 31 may be provided as shown within the balloon inflation lumen 26 and extends the length of the catheter shaft 22 and is provided to improve the torsional and push capabilities of the catheter shaft as is well known to those skilled in the art.

The balloon catheter 21 as shown in FIG. 1 is of a rapid exchange type and is provided with a guide wire lumen 36 which is provided with a flexible elongate member 37 that extends through the distal extremity 24 of the catheter shaft 22 and commences at an opening 38 proximal to the distal extremity 24 of the catheter shaft 22. A conventional guide wire 39 extends through the opening 38 and through the guide wire lumen 36 until it extends beyond the distal extremity 24 of the catheter shaft 22 as shown in FIG. 1. It should be appreciated that in place of a rapid exchange catheter an also conventional over-the-the wire catheter can be used.

A conventional inflatable-deflatable balloon 46 at a diameter of 1.3 mm to 10.0 mm and preferably about 2.5 mm is mounted on the distal extremity 24 of the catheter shaft 22 and is formed of a suitable material such as polyethylene, Nylon, Pebax or PET. It is provided with proximal and distal extremities 47 and 48. The proximal extremity 47 is bonded to the catheter shaft 22 as shown in FIG. 6 by suitable means such as an adhesive. A radiopaque marker 49 is provided on the catheter shaft within the balloon 46 to facilitate positioning of the balloon 46 as hereinafter described. If desired, a pair of radiopaque markers 49 can be provided. The distal extremity 48 of the balloon 46 is bonded to the flexible elongate member 37 by suitable means such as an adhesive to thereby provide a balloon 46 having an interior 53 which is in communication with the balloon inflation lumen 26. The balloon 46 can be inflated and deflated by the use of an inflation device (not shown) secured to the fitting 27. The balloon 46 has an outer or exterior surface 54.

The balloon catheter 21 of the present invention as thus far described is a substantially conventional PTCA balloon. In accordance with the present invention, a plurality of flexible elongate elements 61 extend longitudinally of the balloon 46 the entire length of the balloon 46 and are spaced apart circumferentially of the balloon 46. Typically from one to six flexible elongate elements are utilized. These flexible elongate elements 61 can be in the form of wires or monofilaments formed of a suitable rigid flexible material such as stainless steel, Nitinol, Nylon, fluoropolymer and carbon fiber. Such flexible elongate elements 61 can have a diameter ranging from 0.002" to 0.025". The flexible elongate elements 61 are provided with proximal and distal extremities 62 and 63.

Means is provided for attaching or securing the proximal and distal extremities 62 and 63 of the flexible elongate elements 61 about the catheter shaft in positions spaced longitudinally away from the outer surface 54 of the balloon 46 so that they are slightly in tension. This securement or attachment means can take the form of an adhesive, heat shrink tubing, or by heating the elements to soften the plastic of the balloon so that they will be embedded in the plastic and retained on the outer surface 44 of the balloon and so that they are seated in recesses 66 as shown in FIG. 4. Alternatively, the ends 62 and 63 of the flexible elongate elements 61 can be heated to a melting point and then secured onto the catheter shaft 22 and the flexible elongate member 37 away from the balloon 46.

By way of example the distal extremities 63 of the flexible elongate elements 61 can be secured by UV curable adhesive. The proximal extremities could be secured to the catheter shaft by use of a sleeve of meltable plastic and have placed thereover a sleeve of heat shrinkable material such as PTFE which could be heated to compress the joint while causing melting of the underlying sleeve of a lower melting point material such as Nylon. As soon as the heating has occurred and cooling has taken place, the heat shrinkable sleeve can be removed so that there remains a smooth transition between the catheter shaft 22 and the balloon 46 while affixing the proximal extremities of the flexible elongate elements so that they are at least slightly in tension and are disposed in recesses 66 between flaps or wings 67 of the balloon 46 as shown particularly in FIG. 4. The flaps or wings 67 then can be folded counterclockwise or clockwise to cover the flexible elongate elements to provide a smooth circular outer surface as shown in FIG. 5 to prevent damage to the vessel when the balloon catheter is being introduced into and thereafter advanced in the vessel. A cylindrical balloon protector (not shown) can be slipped over the folded balloon to protect the balloon during shipment and during storage of the balloon catheter.

Operation and use of the balloon catheter of the present invention may now be briefly described as follows. The packaging for the balloon catheter can be removed and the balloon protector slipped off of the balloon. The wrapped balloon with the flexible elongate elements 61 covered thereby is then advanced into the vessel over a guide wire in a conventional manner until it arrives at the stenosis or lesion it is desired to treat. The lesion or stenosis can be a native stenosis or lesion or an in-stent lesion or stenosis. Typically the advancement of the balloon can be ascertained by observing the positioning of the radiopaque markers 49. As soon as the balloon is in the appropriate position, inflation of the balloon can commence by attaching an inflation device (not shown) to the proximal extremity and progressively inflating the balloon 46. As the balloon begins to be inflated, the flaps or wings unfold and then the balloon expands in a radial direction carrying with it the flexible elongate elements 61. The flexible elongate elements 61 are engaged by the outer surface 54 of the balloon and are urged radially outwardly into the stenosis or lesion formed on the vessel wall to create longitudinal channels in the lesion or stenosis. With an appropriate balloon size selection and by selection of a desired pressure as for example 3 to 15 atmospheres, longitudinal channels of the desired size are formed. As the longitudinal channels are formed in the lesion or stenosis, the lesion or stenosis can more easily expand under the pressure from the outer surface of the balloon wall to create the desired flow passage through the lesion or stenosis. Typically, this results in less force being applied to the vessel and less trauma to the vessel in comparison to traditional angioplasty.

If desired, the balloon can be deflated and rotated a predetermined amount and reinflated to form additional longitudinal channels in the stenosis to further aid in expanding the vessel wall.

When the appropriate expansion of the stenosis has occurred, the balloon 46 can be deflated in a conventional manner and the balloon catheter withdrawn from the vessel.

If desirable, a balloon catheter of the present invention of a larger size can then be introduced into the vessel to further increase the size of the opening in the stenosis or lesion in the vessel.

Figure 9:
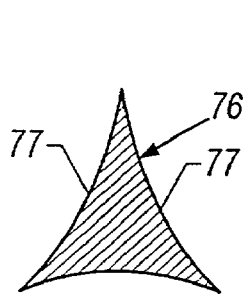
FIG. 9 is an enlarged cross sectional view taken along line 9—9 of FIG. 8.
Figure 10:
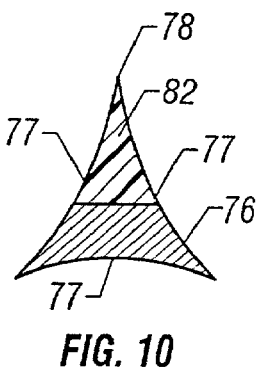
FIG. 10 is an enlarged cross sectional view taken along the line 10—10 of FIG. 8.
Figure 11:
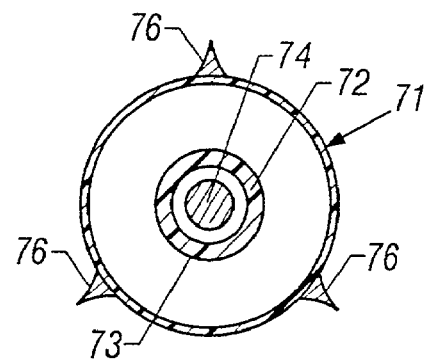
FIG. 11 is an enlarged view in cross section of a balloon catheter incorporating the flexible elongate elements shown FIGS. 8, 9 and 10.

Another embodiment of the invention is shown in FIGS. 8–11. An inflatable-deflatable balloon 71 has been provided which has disposed therein a flexible elongate tubular member 72 having a guide wire lumen 73 therein and in which a guide wire 74 is disposed. As in the previous embodiment of the balloon catheter 21, a plurality of flexible elongate elements 76 are provided which extend longitudinally of the balloon 71 and have proximal and distal extremities (not shown) which can be carried by a catheter shaft (not shown) in the same manner as hereinbefore described. The flexible elongate elements 76 rather than being circular in cross section, as are the flexible elongate elements 61, are generally triangular in cross section. The cross section is in the form of an equilateral triangle with the sides of the triangle being slightly concave to provide outer surfaces which have a curvature generally corresponding to the circumference of the balloon 71. This helps to ensure that the flexible elongate elements 76 will seat properly on the outer surface of the balloon as the balloon is being expanded as shown in FIG. 11.

The flexible elongate elements 76 can be formed with the described cross sectional configuration by suitable means such as drawing the material such as stainless steel or Nitinol through appropriate dies or by profile extrusion in the case of a polymer. The configuration shown in FIGS. 9 and 10 is particularly desirable in that the apex 78 of the triangle is spaced away from the outer surface of the balloon 71 and presents a longitudinal sharp knife-like cutting edge which can enhance the cutting capabilities of the flexible elongate elements during expansion of the balloon 71 to aid in penetrating of the lesion or stenosis to form longitudinal channels therein to facilitate dilation of the passage through the lesion or stenosis in the vessel.

In order to provide enhanced flexibility longitudinally or axially of the flexible elongate elements and of the balloon 71, a plurality of longitudinally spaced apart cutouts 81 are provided in the flexible elongate elements extending downwardly or inwardly from the apex 78 for a suitable distance as for example one-half to two-thirds of the height of the triangular cross section. By way of example as with the flexible elongate elements 61, the flexible elongate elements 76 can have a height ranging from 0.002" to 0.025". The cutouts 81 can have a suitable length as for example ranging from 1 mm to 5 mm and can be spaced apart a suitable distance as for example from 1 mm to 5 mm.

It can be readily appreciated by providing such cutouts 81, the flexibility of the flexible elongate elements 76 with respect to the longitudinal or axial axis to provide axial or longitudinal flexibility to greatly enhance the capability of the balloon catheter to advance through tortuous vessels. The cutouts 81 are filled with a filler 82 of a soft material to not significantly decrease the axial flexibility of the flexible elongate elements. The filler 82 can be of a suitable material such as an adhesive or a polymer. It should be appreciated that the flexible elongate elements 76 can be provided without cutouts if desired, particularly in the case where a polymer is used.

Operation and use of this embodiment of this balloon catheter would be substantially the same as that described for balloon catheter 21.

Figure 12:
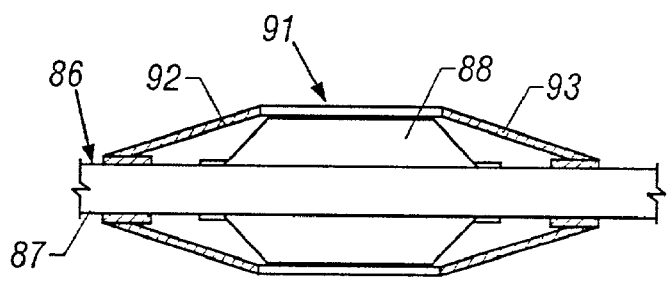
FIG. 12 is another embodiment of a balloon catheter incorporating the present invention in which the proximal and distal extremities of the flexible elongate elements are elastic.

Another embodiment of the balloon catheter incorporating the present invention is shown in FIG. 12. As shown therein, a balloon catheter 86 is provided which includes a catheter shaft 87 of the type hereinbefore described which has mounted on the distal extremity thereof a balloon 88. As in the previous embodiments a plurality of flexible elongate elements 91 extend longitudinally of the balloon 88 and are spaced apart circumferentially of the balloon 88. However, in this embodiment the flexible elongate elements 91 have proximal and distal extremities 92 and 93 which are formed of an elastic material as for example coil springs which will elongate upon expansion of the balloon 88 and retract or recoil upon deflation of the balloon to maintain a substantially constant tension on the flexible elongate elements 91 so that they will remain in close proximity to the outer surface of the balloon 88 during inflation and deflation. These elastic proximal and distal extremities 92 and 93 accommodate changes in length of the flexible elongate elements 91 during expansion and deflation of the balloon. This helps to ensure that the flexible elongate elements 91 will not recess into the balloon during expansion of the balloon. It should be appreciated that rather than having an elastic extremity at both ends of the flexible elongate elements 91, it is only necessary to have at least one elastic extremity by providing only one elastic extremity at either the proximal or distal extremities, but preferably at the proximal extremity.

Figure 13:
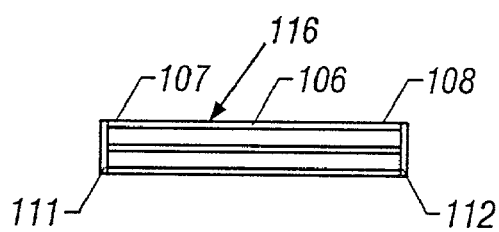
FIG. 13 is an isometric view of a cage incorporating a plurality of flexible elongate elements to be utilized in connection with the balloon catheter of the present invention.
Figure 14:
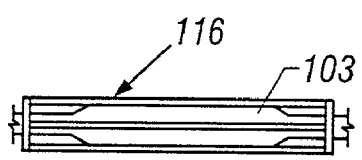
FIG. 14 is an isometric view showing the cage in FIG. 13 mounted on a deflated balloon of a balloon catheter.
Figure 15:
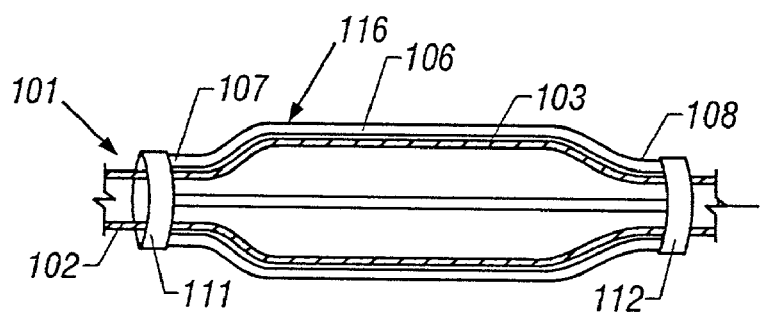
FIG. 15 is an enlarged isometric view showing the position of the cage after the balloon has been moved to an expanded condition.

Still another embodiment of the balloon catheter of the present invention is shown in the balloon catheter 101 in FIGS. 13, 14 and 15. It includes a catheter shaft 102 and an inflatable-deflatable balloon 103 mounted on the distal extremity thereof. A plurality of flexible elongate elements 106 are provided with proximal and distal extremities 107 and 108 which are secured respectively to annuli or rings 111 and 112 by suitable means such as solder to form a cage 116. The annuli or rings 111 and 112 are sized so that they can slip over the balloon 103 when it is in a deflated condition. This permits the cage 116 to be prefabricated and then placed over the balloon after the balloon catheter has been manufactured. The rings 111 and 112 are spaced apart so they will be disposed beyond the opposite ends of the balloon 103 when mounted on the balloon 103. As explained, this cage 116 can be fabricated from separate parts in the manner described or alternatively can be laser cut from a single cylindrical member formed of the desired material or formed with conventional molding techniques where made of a polymer.

Thus as shown in FIG. 14, the cage 116 would be slipped over the balloon 103 while it is deflated and then the flaps or wings (not shown) of the balloon can be folded over the flexible elongate elements 106 in the manner hereinbefore described in the previous embodiments.

The balloon catheter 101 can be positioned in a manner similar to that described for the previous embodiments. After it is in the desired position, the balloon 103 can be inflated to cause expansion of the cage 116 to form longitudinal channels in the lesion or stenosis in the same manner as hereinbefore described. This embodiment of the invention is advantageous in that the cage forms a single piece which cannot readily become dislodged from the balloon during the advancement or retraction of the balloon in the vessel.

It is apparent from the foregoing that there has been provided a new and improved balloon catheter for creating longitudinal channels in lesions and a particularly efficacious method for positioning flexible elongate elements with respect to the balloon to facilitate advancement of the flexible elongate elements into the lesion or stenosis in the vessel being treated without danger from the flexible elongate elements becoming separated from the balloon. A balloon catheter fabricated in this manner is particularly efficacious since it does not require any significant changes in the conventional manufacture of a PTCA balloon.

The invention claimed is:

1. A balloon catheter for performing an angioplasty procedure on a lesion in a vessel comprising a flexible elongate catheter shaft having proximal and distal extremities, a balloon secured to the distal extremity of the catheter shaft and having proximal and distal extremities and having an interior and an inflatable portion movable between deflated and inflated conditions, the catheter shaft having a balloon inflation lumen extending from the proximal extremity to the distal extremity of the catheter shaft and opening into the interior of the balloon, a fitting for supplying an inflation medium to the inflation lumen for causing movement of the inflatable portion of the balloon from the deflated condition to the inflated condition, the inflatable portion of the balloon having an outer surface which moves outwardly radially upon inflation of the balloon and at least one flexible elongate element extending over the outer surface of the balloon from the proximal extremity to the distal extremity of the balloon, said flexible elongate element having a proximal extremity coupled to the catheter shaft proximal of the inflatable portion of the balloon and a distal extremity, an elastic member distinct from the flexible elongate element for coupling the distal extremity of the flexible elongate element to the catheter shaft distal of the inflatable portion of the balloon and for permitting the flexible elongate element to move radially outward as the balloon is inflated whereby expansion of the balloon causes movement of the flexible elongate element into engagement with the lesion to form a longitudinal channel in the lesion.

2. A balloon catheter as in claim 1 wherein a plurality of flexible elongate elements are provided which are spaced apart circumferentially of the balloon.

3. A balloon catheter as in claim 1 wherein the elastic member is formed of an elastic material to permit outward radial movement of the flexible elongate element during inflation of the balloon.

4. A balloon catheter as in claim 1 wherein said balloon when in a deflated condition is folded over the flexible elongate element to prevent injury to the vessel during delivery of the balloon to the lesion in the vessel.

5. A balloon catheter as in claim 1 wherein said flexible elongate element is substantially circular in cross section.

6. A balloon catheter as in claim 1 wherein said flexible elongate element is substantially triangular in cross section.

7. A balloon catheter as in claim 6 wherein said outer surface of the balloon in the inflated condition in cross section has a curved surface and wherein said flexible elongate element which is triangular in cross section has a surface in cross section which is concave to accommodate the curved outer surface of the inflated balloon and to provide a better fit between the balloon and the flexible elongate element as the balloon is expanded to bring the flexible elongate element into engagement with the lesion in the vessel.

8. A balloon catheter as in claim 6 wherein said flexible elongate element has a longitudinal axis and has longitudinally spaced apart cutouts therein to increase the flexibility of the flexible elongate elements along the longitudinal axis.

9. A balloon catheter as in claim 8 wherein filler material is disposed in the cutouts.

10. A balloon catheter as in claim 9 wherein said filler is a relatively soft material selected from a group consisting of an adhesive and a polymer.

11. A balloon catheter as in claim 1 wherein said flexible elongate element is formed of a rigid flexible material selected from a group consisting of stainless steel, Nitinol, Nylon, fluoropolymer and carbon fiber.

12. A balloon catheter as in claim 1 wherein the flexible elongate element is detached from the outer surface of the balloon.

13. A balloon catheter for use with an inflation medium to perform an angioplasty procedure on a lesion in a vessel comprising a flexible elongate catheter shaft having proximal and distal extremities, a balloon secured to the distal extremity of the catheter shaft and having an inflatable portion provided with an interior, the catheter shaft having a balloon inflation lumen extending from the proximal extremity to the distal extremity and opening into the interior of the balloon adapted to supply the inflation medium to the interior so as to permit inflation of the balloon, and at least one flexible elongate element secured to the catheter shaft proximal and distal of the inflatable portion so as to extend longitudinally over the inflatable portion of the balloon and be in longitudinal tension over the inflatable portion of the balloon whereby upon inflation of the balloon the flexible elongate element is moved into engagement with the lesion to form a longitudinal channel in the lesion.

14. A balloon catheter as in claim 13 wherein a plurality of flexible elongate elements are provided which are spaced apart circumferentially of the balloon.

15. A balloon catheter as in claim 13 wherein the flexible elongate element has proximal and distal extremities, at least one of the proximal and distal extremities of the flexible elongate element being formed of an elastic material to permit stretching of the flexible elongate element during inflation of the balloon.

16. A balloon catheter as in claim 15 wherein both of the proximal and distal extremities of the flexible elongate element are formed of an elastic material.

17. A balloon catheter for use with an inflation medium to perform an angioplasty procedure on a lesion in a vessel comprising a flexible elongate catheter shaft having proximal and distal extremities, a balloon secured to the distal extremity of the catheter shaft and having an inflatable portion provided with an interior, the catheter shaft having a balloon inflation lumen extending from the proximal extremity to the distal extremity and opening into the interior of the balloon adapted to supply the inflation medium to the interior so as to permit inflation of the balloon, and at least one flexible elongate element formed from a material and having a proximal extremity secured to the catheter shaft proximal of the inflatable portion and a distal extremity secured to the catheter shaft distal of the inflatable portion whereby upon inflation of the balloon the flexible elongate element is moved into engagement with the lesion to form a longitudinal channel in the lesion, at least one of the proximal and distal extremities of the flexible elongate element being formed of an elastic material distinct from the material of the remainder of the flexible elongate element to permit stretching of the flexible elongate element during inflation of the balloon.

18. A balloon catheter as in claim 17 wherein both of the proximal and distal extremities of the flexible elongate element are formed of the elastic material.

19. A balloon catheter as in claim 17 wherein a plurality of flexible elongate elements are provided which are spaced apart circumferentially of the balloon.

20. A balloon catheter for performing a medical procedure on a lesion in a vessel comprising a flexible elongate catheter shaft having proximal and distal extremities, a balloon secured to the distal extremity of the catheter shaft and having an inflatable portion provided with an interior, the catheter shaft having a balloon inflation lumen extending from the proximal extremity to the distal extremity and opening into the interior of the balloon for supplying an inflation medium to the interior of the balloon so as to cause the inflation portion of the balloon to move radially outward and at least one flexible elongate element extending over the inflatable portion of the balloon and having first and second extremities, the first extremity of the flexible elongate member being coupled to the catheter shaft, an elastic member distinct from the flexible elongate member for securing of the second extremity of the flexible elongate member to the catheter shaft for permitting the flexible elongate member to move radially outward as the balloon is inflated.

21. The balloon catheter of claim 20 wherein upon inflation of the balloon the flexible elongate element is moved into engagement with the lesion.

22. The balloon catheter of claim 20 wherein the balloon has first and second end portions, the first extremity of the flexible elongate member being coupled to the catheter shaft in the vicinity of the first end portion of the balloon and the elastic member securing the second extremity of the flexible elongate member to the catheter shaft in the vicinity of the second end portion of the balloon.

23. The balloon catheter of claim 20 wherein the elastic member secures the second extremity of the flexible elongate member to the catheter shaft distal of the inflation portion of the balloon.

24. The balloon catheter of claim 20 wherein the elastic member secures the second extremity of the flexible elongate member to the catheter shaft proximal of the inflation portion of the balloon.

25. The balloon catheter of claim 20 wherein the elastic member is a coil spring.

* * * * *